United States Patent [19]

Nelson et al.

[11] Patent Number: 4,826,488
[45] Date of Patent: May 2, 1989

[54] HYPODERMIC SYRINGE NEEDLE GUARD

[76] Inventors: Robert A. Nelson, 13417 Beaver St., Sylmar, 91342; Robert C. Flome, 15805 St. Timothy Rd., Apple Valley, both of Calif. 92307

[21] Appl. No.: 162,035

[22] Filed: Feb. 29, 1988

Related U.S. Application Data

[63] Continuation of Ser. No. 19,642, Feb. 27, 1987, Pat. No. 4,735,617, which is a continuation of Ser. No. 796,280, Nov. 8, 1985, Pat. No. 4,659,330.

[51] Int. Cl.⁴ ............................................. A61M 5/32
[52] U.S. Cl. ................................... 604/192; 604/198
[58] Field of Search ................ 604/192, 263, 198, 187

[56] References Cited

U.S. PATENT DOCUMENTS 4,717,386 1/1988 Simmons ............................. 604/192

Primary Examiner—John D. Yasko
Attorney, Agent, or Firm—David O'Reilly

[57] ABSTRACT

A guard for a hypodermic syringe needle which keeps the extremities and particularly the hands well away from the syringe to prevent accidental punctures with contaminated needles. The needle guard is in the form of a cylindrical cap which slides over the needle having a manipulating device to remove and replace the guard while keeping the hands well away from the needle. In one embodiment the manipulating device is in the form of a flexible handle for removing the cap. As an alternative the end of the needle guard can be flared to provide a flat surface for receiving an adhesive. The needle is then removed by pressing the adhesive base to any convenient surface. The needle guard is replaced by simply inserting the needle in the guard and snapping the guard from the surface by giving the syringe a quick twist when the cap is fully seated over the needle.

8 Claims, 2 Drawing Sheets

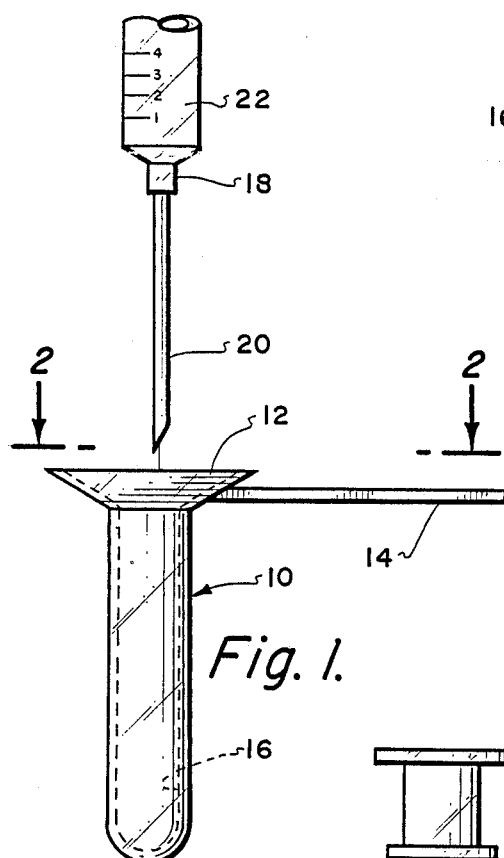
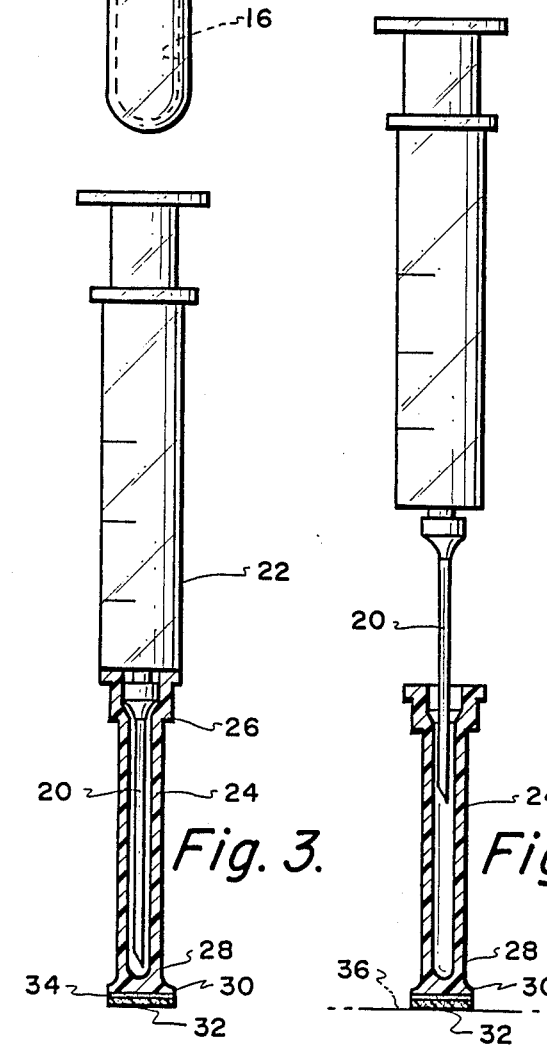
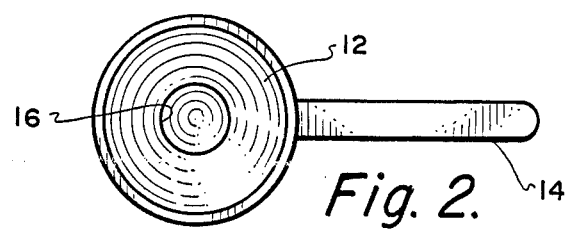
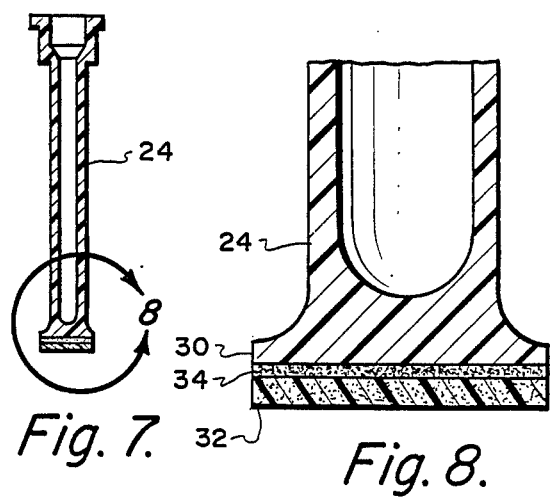
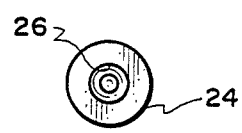

HYPODERMIC SYRINGE NEEDLE GUARD

This application is a continuation of Ser. No. 019,642 filed Feb. 27, 1987 now U.S. Pat. No. 4,735,617 which is continuation-in-part of application Ser. No. 796,280 filed Nov. 8, 1985, now U.S. Pat. No. 4,659,330

FIELD OF THE INVENTION

This invention relates to hypodermic syringes and more particularly relates to methods to prevent accidental puncture with contaminated needles on hypodermic syringes.

BACKGROUND OF THE INVENTION

Hypodermic syringes of known constructions employ a cylindrical barrel having a needle covered with an end cap. To use the syringe, the end cap is slipped off and the needle inserted into a patient to inject a fluid with a plunger or aspirate blood and other bodily fluids back into the syringe. After use the cap is replaced on the needle and both are discarded. A not infrequent problem with these devices however is the accidental puncture of the medical attendant using the syringe when replacing the cap. Often this occurs when the cap is being replaced and requires care to be sure the needle is properly inserted in the cap. If a distraction occurs the user can easily miss the entrance to the cap and puncture the finger or some other portion of the hand or arm. Since these needles are frequently used on patients that have serious blood borne diseases the contamination can be transferred to the medical attendant infecting them with the disease of the patient. This can have serious side affects if the disease is an infectious disease such as hepatitis, aids or other infectious diseases. It would be advantageous if some method could be provided for replacement of a protective cap on the needle while keeping the extremities and particularly the hands well away from the needle point.

Examples of caps for hypodermic syringe needles are shown in U.S. Pat. Nos. 2,408,323, 2,571,653, 3,073,306, 3,527,216, 3,890,971, 4,355,822, 4,373,526 and 4,425,120, all show a slideable shield to protect the needle on a hypodermic syringe. Each of these devices is quite complex and requires special manufacture of the hypodermic syringe. To date none of these devices appear to be on the market for reasons which should be apparent from an examination of the patents. U.S. Pat. Nos. 3,825,003, 3,976,069 and 4,249,530 all show caps which act as needle guards. None of the devices appear to show a simple, easy to manufacture protective cap which can be used with existing syringes and needles.

SUMMARY OF THE INVENTION

The purpose of the present invention is to provide a protective cap or covering for the needle of a hypodermic syringes to prevent infection from accidental punctures of medical personnel using the syringe.

The purpose of the present invention is to provide the above features in the simplest, most economical manner with a device substantially adaptable to existing syringes and needles. In one embodiment the usual end cap fitted over the hypodermic needle has an arm extension for removing and replacing the cap.

In another modified version of the present invention the needle cap, fitted over the hypodermic needle, has its base or end of the cap flattened to be wider than the sheath diameter that receives the needle to provide a stable base. The flattened base is provided with bonded adhesive material. The adhesive tip or end as thus provided allows the end cap to be removed from the needle by pressing the adhesive on the base to any conveniently flat surface. The needle attached to the syringe now can easily and safely be returned to the needle cap while keeping the fingers or hand from being near the pointed end of the needle. That is, the cap need not be held with the other hand. The needle is simply guided by the hand holding the syringe into the end cap aperture until fully seated and the cap removed from the surface with a quick twist and pull. Thus the serious problem of being stuck with contaminated needles is avoided.

The syringe may now be used in the usual fashion of injecting the needle and discharging the contents of the syringe through the needle. Additionally the needle and end cap may be removed from the syringe and discarded if medical personnel are to perform an arterial blood gas procedure that requires the removal of the needle from the syringe to facilitate introduction of a blood sample into a blood gas analyzer.

As a further alternative, a slideable sheath or sleeve could be provided which slips over existing syringes and protective end caps which remains in an extended position until ready for use. The sleeve is then slid back to expose the protective end cap which can be pulled off and discarded or put back in place if desired. The end cap may also have a broad end or base with an adhesive allowing removal with one hand by pressing the adhesive against a convenient flat surface. The syringe may now be used and after use the sleeve extended to cover and protect against any punctures from an exposed contaminated needle with the cap replaced if desired. The advantage of the latter design is that the sleeve can be simply provided as an accessory to existing syringes which simply slides over and snaps onto the syringe barrel or cylinder. A tear-off protective cover closes the end of the sleeve. This seals the entire area around the needle and protective end cap. Preferably the sleeve is adaptable to existing, in use syringes with end caps while at the same time providing the medical attendant or user from protection against a puncture with a contaminated needle. Thus in each of the embodiments described above these features are met with a simplicity of design which minimizes their cost while maximizing their convenience and protection.

It is therefore one object of the present invention to provide a hypodermic syringe needle guard which is simple in construction and easy to use.

Yet another object of the present invention is to provide a needle guard which does not deviate substantially from existing technology for needle protection. Instead it uses the existing technology to provide a needle guard by adapting generally used needle guards for protection by adding a small feature or adding a part which does not modify the existing structure.

Yet another object is to provide a needle protective end cap for a syringe with a flat adhesive tipped end which can be removed and replaced in a one hand operation.

The above and other features of the invention will be more fully understood from the following detailed description and the accompanying drawings, in which:

BRIEF DESCRIPTION OF THE DRAWINGS

FIG. 1 is a side elevation of a very simple cap protection device according to the invention.

FIG. 2 is a view taken at 2—2 of FIG. 1.

FIG. 3 is a alternate embodiment of the invention in which the end cap has an adhesive tip.

FIGS. 4 and 5 illustrate removal of the protective end cap of the embodiment of FIG. 3.

FIG. 6 is a view taken at 6—6 of FIG. 5.

FIG. 7 is a side elevation of the adhesive tipped end cap of FIG. 3.

FIG. 8 is an enlarged view taken at 8 of FIG. 7.

DETAILED DESCRIPTION OF THE INVENTION

Figure 9:
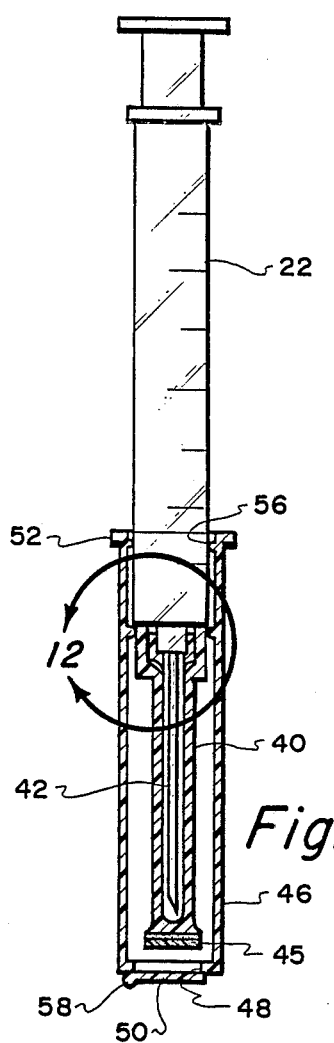
FIG. 9 illustrates yet another embodiment of the invention including a slideable protectable sleeve in conjunction with protective end cap.
Figure 10:
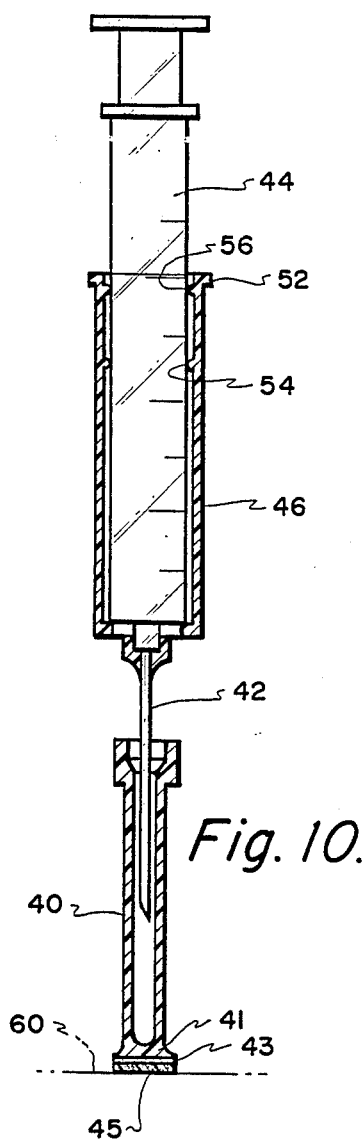
FIG. 10 illustrates the operation of the device of FIG. 9.
Figure 11:
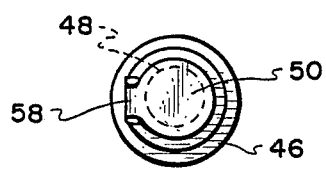
FIG. 11 is a bottom view of the embodiment of FIG. 9.
Figure 12:
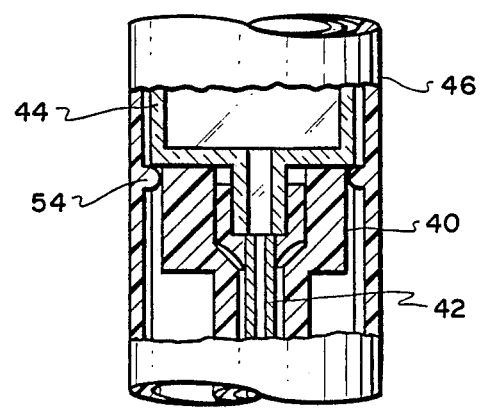
FIG. 12 is a detailed sectional view taken at 12 of FIG. 9.

The simplest form of protection for a needle guard is illustrated in FIGS. 1 and 2. In this embodiment the protective end cap is in the form of an elongated cap 10 having a funnel shaped collar 12 and arm extension 14. Cap 10 has a hollow interior at 16 which tightly fits neck 18 at the upper end of needle 20.

Medical personnel using the hypodermic syringe grasps arm extension 14 or cap 10 to pull the protective cap away from needle 20 exposing the needle for use. After use the cap is replaced by holding extension 14 so that funnel shaped collar 12 prevents mishaps by assuring that the end of needle 20 is guided into cavity 16 in the cap.

The embodiment in FIG. 1 is simple in construction but has the disadvantage that arm extension or handle 14 extends outward from the cap making, packaging, shipping and storing a problem. For this reason the alternate embodiment of FIGS. 3 through 8 were conceived. In this embodiment a tubular cap 24 is provided to cover needle 20 attached to body 22 of the syringe. Cap 24 is held in place by a tight frictional fit at 26.

As indicated previously a continuing serious problem of contamination occurs to medical personnel when replacing the cap on needles. The embodiment of FIGS. 1 and 2 allows the user to hold the cap by tab 14 and insert the needle 20. However, even in this embodiment there is the danger of puncture because one hand must be in the general vicinity of the needle when replacing the cap. Since it obviously would be advantageous if the cap can be replaced by plunging the needle into the cap without having any hand or extremity anywhere near the end of the needle the embodiments of FIGS. 3 through 12 were conceived.

Referring to FIGS. 3 through 6 cap 24 is provided with a tight frictional fit at 26 to be secure on needle 20. However, in this embodiment end portion 28 is provided with a substantially flattened circular base 30 to which an adhesive 32 is secured by bonding material 34. This is shown in greater detail in the partial sectional view of FIG. 8. Cap 24 is flattened and broadened at 30 to provide a flat smooth surface for attachment of an adhesive 32 bonded at 34 to the base provided by flattened area 30. The adhesive 32 itself may if desired also serve as the bonding agent. However, it is preferable that the adhesive 32 be the type of material that will stick to almost any surface but can be easily lifted off. Adhesives that can temporarily be pressed to fasten something to a surface but easily removed are readily available in the art. An adhesive such as a hot melted resin, a rubber based tape, or a hook and loop material commonly known as Velcro would be suitable. Also if desired a peel-off protective covering (not shown) can be placed over the end of the adhesive material 32 until ready for use. The covering would serve to retain the adhesiveness of the material for a substantial period of time.

When using the syringe 22 having the adhesive mounted cap 24, the cap is simply pressed on any, surface, indicated at 36 preferably flat and the needle 20 withdrawn. The adhesive 32 is sufficiently sticky to retain the cap upright on the surface to which it is attached. Suitable adhesives will stick to almost any surface available. Preferably an adhesive which will temporarily stick to blankets, bedding or nightstands available in all medical facilities will be used. After using the syringe the attendant would simply replace the needle 20 by plunging the needle 20 into the open end 38 of the cap 24. This is simply a reverse of the process for removing the needle. A slight twisting or snapping motion will easily separate the adhesive 32 from the surface 36. Thus in the manner described medical personnel do not have to hold the cap 24 when replacing it on the needle 20. Hands and arms can thus be kept well away from the tip of the needle 20 preventing accidental puncture and contamination.

Another embodiment which utilizes the principals of the embodiment of FIGS. 3 through 8 is illustrated in FIGS. 9 through 12. The advantage of this embodiment is that it can be adapted to a standard syringe having a snap-on protective end cap 40 covering needle 42 attached to standard syringe body 44 of a hypodermic syringe or cap having an adhesive end 45 as described in the embodiments of FIGS. 3 through 8. The cap 40 may be a simple pull-off type cap supplied with standard hypodermic disposal syringes. To this configuration is added sleeve 46 having opening 48 covered by a adhesive secured membrane 50 as can be seen more clearly in FIG. 11. The sleeve 46 is a simple hollow cylinder having a gripping flange 52 at the upper end and aperture 48 sufficiently large to clear the protective cap 40 when the sleeve 46 is retracted. The sleeve is secured to the cylindrical body 44 of the syringe by a circumferential ribs 54 and 56 on the inside surface of sleeve 46. Upper circumferential rib 56 frictionally retains sleeve 46 on the body 44 while lower rib 54 retains sleeve 46 in an extended position shown in FIG. 12 covering end cap and needle 40 and 42, respectively.

Alternatively cap 40 can be modified to provide a flared base 41 to which is added an adhesive 45 bonded at 43 as before. The flared base 41 should be small enough in diameter to easily pass through aperture 48 after removal of membrane cover 50.

In use sheath or sleeve 46 is drawn back on hypodermic syringe body 44 after removal of protective membrane 50 by pulling tab 58. Protective end cap 40 may now be removed in the usual manner and either discarded or retained for replacement after use if desired.

The needle is now exposed for injection and discharging the contents of the syringe or for withdrawing fluid from a patient. After use, sleeve 46 is slid downward by grasping and pushing downward on flange 52 until rib 54 passes beyond the end of body 44 with the sleeve completely covering and protecting needle 42. Needle cap 40 can be safely inserted through the opening 48 and pushed back on needle 42 if the syringe is to be used in a procedure such as an arterial blood gas analysis.

If the adhesive end 45 is used cap 40 may be readily stuck to any convenient surface 60 for later replacement by inserting the needle 42 into the open end of the cap 40. A quick twist on the syringe will separate the adhesive 45 from the surface 60 and the sheath 46 may now be extended to cover the needle and cap as shown in FIG. 9.

As can be seen in the last embodiment the sleeve is adaptable to existing syringes by simply inserting the sheath over the existing end cap engaging the body of the syringe. This makes the device very economical to manufacture and adapt to existing syringes having protective needle end caps 40.

Thus there has been disclosed a tipped needle guard embodiment manipulating device in the form of a needle cap whose base is wider than the cylindrical body of the barrel and has a flat flared end surface upon which is bonded a suitable adhesive material such as a hot melt resin, or a rubber base tape. The clinician after having removed the end cap from the syringe can proceed to temporarily attach the end cap to any convenient surface such as wood, metal or clothing complete the medical procedure and return the contaminated needle back to the guard or end cap that is safe and easy to do. This is accomplished by simply inserting the needle back into the end cap without holding the end cap and with a quick twist serparating the adhesive from the surface.

This invention is not to be limited by the embodiment shown in the drawings and described in the description which is given by way of example and not of limitation but only in accordance with the scope of the appended claims.

What is claimed is:

1. A hypodermic syringe needle guard comprising; shield means for shielding said needle; said shield means comprising;
   a hollow cylindrical cap having an open end and a closed end adapted to fit around said needle and be frictionally retained on a syringe;
   said closed end of said hollow cylindrical cap terminating in an end forming a base;
   adhering means bonded to said end forming a base of said hollow cylindrical cap;
   removing and replacing means on said hollow cylindrical cap for removing and replacing said hollow cylindrical cap;
   said shield including a hollow cylindrical sleeve slidably retained on said syringe, said sleeve when extended surrounding said needle with or without said hollow cylindrical cap; said hollow cylindrical sleeve having an aperture at its end remote from said syringe through which said hollow cylindrical cap may pass; and an adhesively retained membrane covering said aperture for sealing said aperture for sealing said hollow cylindrical sleeve around said cylindrical cap and needle until ready for use;
   whereby said membrane may be peeled off and said hollow cylindrical sleeve retracted to expose said cylindrical cap and needle for use and extended after use to cover said needle with or without replacement of said cylindrical cap.

2. The needle guard according to claim 1 in which said adhesive is selected from the group consisting of hot melt resin or a rubber base tape.

3. The needle guard according to claim 1 including a circumferential rib on the interior surface of said sleeve for frictionally retaining said sleeve on said syringe.

4. The needle guard according to claim 1 in which said adhesive is selected from the group consisting of hot melt resin or a rubber based tape.

5. The needle guard according to claim 1 in which;
   said closed end of said hollowing cylindrical cap terminates in a flattened surface forming a base;
   said adhering means being bonded to said flattened end surface of said hollow cylindrical cap;
   whereby said hollow cylindrical cap may be removed from said syringe needle and attached to any convenient available surface for easy replacement while keeping the hands away from said needle.

6. A hypodermic syringe needle guard comprising; shield means for shielding said needle; said shield means comprising;
   a hollow cylindrical cap having an open end and a closed end adapted to fit around said needle and be frictionally retained on a syringe;
   said closed end of said hollow cylindrical cap terminating in an end forming a base;
   adhering means bonded to said end forming a base of said hollow cylindrical cap;
   removing and replacing means on said shield for removing and replacing said shield;
   a hollow cylindrical sleeve slidably retained on said syringe, said sleeve when extended surrounding said needle with or without said cylindrical cap;
   whereby said cylindrical sleeve may be retracted to expose said hollow cylindrical cap for removal from said syringe needle and attachment to any convenient available surface for easy replacement while keeping the hand away from said needle.

7. A hypodermic syringe needle guard comprising;
   a hollow cylindrical cap having an open end and a closed end adapted to fit around said needle and be frictionally retained on a syringe; said closed end of said hollow cylindrical cap constructed to form a base; adhering means securely attached to said base on the closed end of said cylindrical cap; said adhering means constructed to retain said hollow cylindrical cap on a conveniently located surface;
   whereby said hollow cylindrical cap may be removed from said syringe needle and attached to any convenient available surface for easy replacement while keeping the hands away from said needle.

8. The invention according to claim 7 wherein said adhering means comprises a Velcro type material securely bonded to said base on said hollow cylindrical cap.

* * * * *